United States Patent [19]

Anifrani et al.

[11] Patent Number: 5,554,810
[45] Date of Patent: Sep. 10, 1996

[54] METHOD FOR THE PREDICTIVE DETERMINATION OF LOAD OF A STRUCTURE AT RUPTURE

[75] Inventors: Jean-Charles Anifrani, Saint Medard en Jalles; Christian M. Le Floc'h, Blanquefort; Didier Sornette, Nice; Bernard Souillard, Le Chesnay, all of France

[73] Assignee: Aerospatiale Societe Nationale Industrielle, Paris Cedex, France

[21] Appl. No.: 380,617

[22] Filed: Jan. 30, 1995

[30] Foreign Application Priority Data

Jan. 31, 1994 [FR] France .................................. 94 01237

[51] Int. Cl.⁶ .................................................. G01N 29/04
[52] U.S. Cl. .................................................. 73/801; 73/587
[58] Field of Search ........................................ 73/587, 801

[56] References Cited

U.S. PATENT DOCUMENTS

| | | |
|---|---|---|
| 3,545,262 | 12/1970 | Steele et al. . |
| 4,140,021 | 2/1979 | Nomura et al. . |
| 4,468,965 | 9/1984 | Blackburn . |
| 4,577,487 | 3/1986 | Dooley . |
| 4,641,526 | 2/1987 | Izumi et al, ................ 73/587 |
| 4,732,045 | 3/1988 | Blackburn . |
| 4,979,124 | 12/1990 | Sachse et al. ............... 73/587 |
| 5,029,474 | 7/1991 | Schulze ....................... 73/587 |
| 5,142,916 | 9/1992 | Yamaguchi ................. 73/587 |

FOREIGN PATENT DOCUMENTS 0279431  8/1988  European Pat. Off. .

OTHER PUBLICATIONS

French Search Report and Annex Jul. 21, 1994.

*Primary Examiner*—Richard Chilcot
*Assistant Examiner*—Max Noori
*Attorney, Agent, or Firm*—Greenblum & Bernstein P.L.C.

[57] ABSTRACT

Method for predictive determination of load, simple or combined, at rupture, of a structure, which includes subjecting the structure to a stress which is equivalent to the load; recording acoustic activity generated by damages suffered in the structure, up until a pre-determined stress threshold; and determining the predictive value of the load at rupture using the recorded acoustic emission based on a relationship linking time to the load.

13 Claims, 2 Drawing Sheets

METHOD FOR THE PREDICTIVE DETERMINATION OF LOAD OF A STRUCTURE AT RUPTURE

BACKGROUND OF THE INVENTION

The present invention is related to a pre-rupture prediction of a structure's load at rupture.

The term structure designates a finished material body, homogeneous or heterogeneous, designed to resist predetermined physical stresses, known here by the term load, which can be both simple or combined. The object of the invention is to predict the endurance limit of the body with respect to the load.

Although the invention can find an application in many types of structures, it will be described herein with reference to its application as regards the inspection of storage tanks for gas under high pressure, and especially as regards the inspection of tanks made of a composite material wound on a metallic liner.

Such tanks, generally spherical, and intended to withstand internal pressures that are capable of reaching or exceeding 800 bars, are subject to non-destructive inspections among which is included inspection by acoustic emissions.

This technique, whose object is to check the well being of the metal and of the composite material, consists of subjecting the tank to be tested to a predetermined pressure stress, which causes irreversible microscopic damages in the materials, the appearance thereof releasing energy in the form of thermal or acoustic energy. Only the acoustic energy, which is easier to use, is detected by means of piezo-electrical sensors and enables any fault in progress to be detected.

Thus, in the course of a test cycle involving incremental pressure up until a maximum predetermined pressure, typically the acoustic emissions are recorded at the design pressure, that is 1.5 times the working pressure of the tank.

An analysis of these acoustic emissions on the basis of pre-established criteria enables one to declare whether the tank is able or unable to fulfill its mission.

It is clear that this technique, although enabling the detection and even the localization of faults in the tested tank, does not provide any indication as regards the effective value of the pressure at rupture, which is necessarily greater than the design pressure.

Up until now, there is no check that can quantify, for each tank, the predictable level of pressure at rupture, which forces one, due to reasons of reliability, to apply safety coefficients that inevitably lead to oversized installations. These oversized installations lead to, especially for structures made of expensive materials, such as the tanks mentioned hereinabove, for aeronautical or space-related use, prohibitive increases in weight and cost.

SUMMARY OF THE INVENTION

It is the object of the present invention to reduce this oversizing while at the same time reinforcing the operational safety of such structures by suggesting a non-destructive, precise and individual evaluation technique for each structure as regards its effective endurance limits with respect to the stresses that it must face and in consideration whereof it was designed and built.

To this end, the object of the invention is a method for the predictive determination of the load, simple or combined, at rupture, of a structure, characterized in that it consists of subjecting the structure to a stress of the same type as the load and which is time dependent as per a predefined law, while at the same time recording the acoustic activity generated by the damages suffered, up until a predetermined stress threshold and to thereafter use the recorded acoustic emission on the basis of the following relationship:

$dE/dt = Eo/(t_r - t)^\alpha$ in which:

dE/dt is the variation of acoustic energy generated by said damages;

Eo is said to be a standardizing factor;

t is time, and $t_r$ is the moment of rupture, the exponent $\alpha$, Eo and $t_r$ being determined on the basis of the relationship $$\text{Log } (dE/dt) = -\alpha \text{ Log } (t_r - t) + \text{Log } (Eo),$$

in order to determine the predictive value of the load at rupture on the basis of the pre-established law linking time to the load.

In its application to a structure constituted by a tank made of a composite material wound on a metallic liner, the method is implemented, for example, by bringing the tank to an internal testing pressure as per a predetermined protocol.

BRIEF DESCRIPTION OF THE DRAWINGS

Other characteristics and advantages will become apparent from the description that follows of an embodiment of the method as per the invention, such description being provided only as an example and with reference to the annexed drawings wherein.

DETAILED DESCRIPTION OF THE PREFERRED EMBODIMENTS

Figure 1:
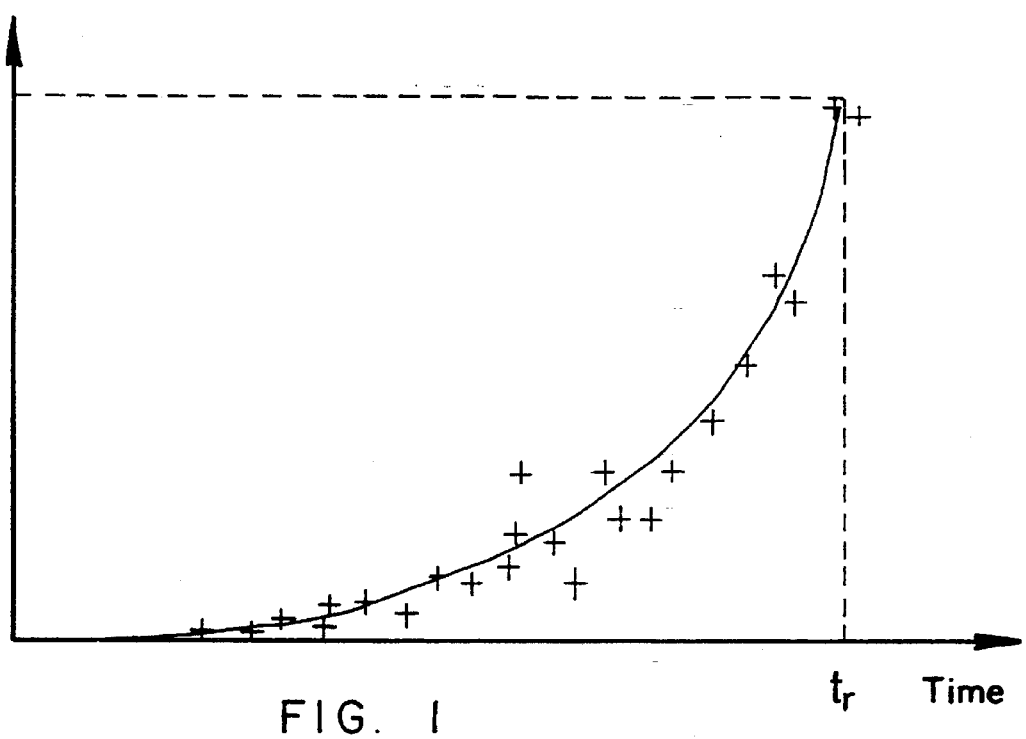
FIG. 1 represents the variation over time, expressed in the number of hits, of the acoustic energy generated when a tank is placed under pressure.

Acoustic emission is a non-destructive inspection technique that has been used for a number of years for the acceptance, for example, of storage tanks for gas under high pressure used to equip satellites.

This technique consists of recording the signals emanating from the irreversible damages when a structure, for example, a tank, is subject to load.

The materials subject to stress suffer damages, that are accompanied by, when they are generated, by a release of energy, both thermal and acoustic.

Energy of the thermal type is usually too weak to be detected, whereas acoustic energy can be easily detected by appropriate equipment, usually constituted, for example, for a structure of the tank type made of a composite material wound on a metallic liner, of piezo-electrical sensors adhered by means of a coupler to the surface of the composite material. Indeed, the acoustic energy emanating from a localized damage, such as a matrix microcracking, delamination or fiber ruptures, gets propagated through the material until it reaches the surface where the acoustic waves are detected by the piezo-electrical sensors.

Since the damage incurred is an irreversible phenomenon, the associated acoustic emission is also irreversible. The technique of acoustic emission, that only detects faults in progress, said faults alone producing acoustic waves, thus records the history of the structure, in other words, its behavior over time during variations in the applied stresses.

Said piezo-electrical sensors provide electrical signals that are thereafter amplified and processed.

Signal processing consists mainly of detecting events and counting those that exceed a predetermined threshold. These threshold exceeding signals, or hits, are added cumulatively, as rates or even as amplitudes and represent acoustic activity, the recording of such activity being done in accordance with the load parameters, for example, the pressure for the tanks.

In order to obtain overall information regarding the irreversible damage, or in other words the faults in progress, the structure must be stressed at an adequate level and generally be subjected to a test cycle using incremental applied force.

Acoustic monitoring during each incremental force enables one to detect if the acoustic emission activity is decreasing, in which case the structure adapts to the stress, or conversely, if such activity is increasing substantially, in which case one is in the presence of an avalanche process that could lead to the destruction of the structure.

Such a technique enables one to obtain qualitative information as regards the state of health of the structure thus inspected.

It also enables one to obtain quantitative information regarding load at rupture, but this is an empirical process that aims to establish the criteria that characterize the approach of the rupture.

This process involves reconducting an experimental analysis at each change of shape, scale or material of the structure to be tested, so as to adjust the criteria. For these reasons, this approach can neither be used industrially, and nor is it sufficiently reliable.

The approach as per the instant invention is based on establishing a statistical physical model that takes into account, not the average behavior, but the fluctuations that in some way constitute the signature of the dominant effects, often working in tandem, that lead directly to the rupture.

Such a model, based on the theory of percolation and the theory of rupture, results in, as per the invention, the structure, such as a tank, being subject to an increased load that is time dependent as per a predefined law and to a recording of the acoustic energy released by the damages, to linking to time the variation in the recovered acoustic energy as per the law of exponents:

$dE/dt = Eo/(t_r - t)^\alpha$ in which:

dE/dt is the variation of acoustic energy generated by the damages;

Eo is said to be a standardizing factor;

t is time, and $t_r$ is the moment of rupture,

In Log-Log coordinates, the above relationship can be expressed by:

$Log\ (dE/dt) = -\alpha\ Log\ (t_r - t) + Log\ (Eo)$,

This relationship is none other than the equation of a perpendicular whose slope directly results in the exponent $\alpha$.

Thereafter, the method as per the invention will consist of subjecting the tank to an increased load that is time dependent as per a pre-defined law, while at the same time recording the acoustic activity generated by the damages suffered, up until a predetermined pressure threshold, that is less than the rupture pressure, and to determine, by calculation, on the basis of the relationship:

$dE/dt = Eo/(t_1 - t)^\alpha$ in which:

dE/dt is the variation of acoustic energy generated by the damages;

Eo is said to be a standardizing factor;

t is time, and $t_r$ is the moment of rupture, the exponent $\alpha$, Eo and $t_r$ being determined from the relationship $Log\ (dE/dt) = -\alpha\ Log\ (t_r - t) + Log\ (Eo)$, the predictive value of the load at rupture from a pre-established law linking time to the load.

During the research and analyses carried out within the scope of the invention, it was demonstrated that there was, in tests undertaken in spherical tanks constituted of a composite Kevlar or carbon and epoxy resin winding on a titanium liner, and subjected to a monotonous increase in pressure until rupture, with a recording of the acoustic activity, a change over time in the variation of energy dE/dt generated by the acoustic emissions having a curve path in the law of exponents.

In FIG. 1 is illustrated such a curve obtained from the cumulated value in the number of hits of the acoustic energy dissipated bit by bit from the rupture process over time, $t_r$ being the time of rupture of the tank.

The modelized translation of this curve into exponential law is expressed by the relationship disclosed hereinabove:

$dE/dt = Eo/(t_r - t)^\alpha$

Figure 2:
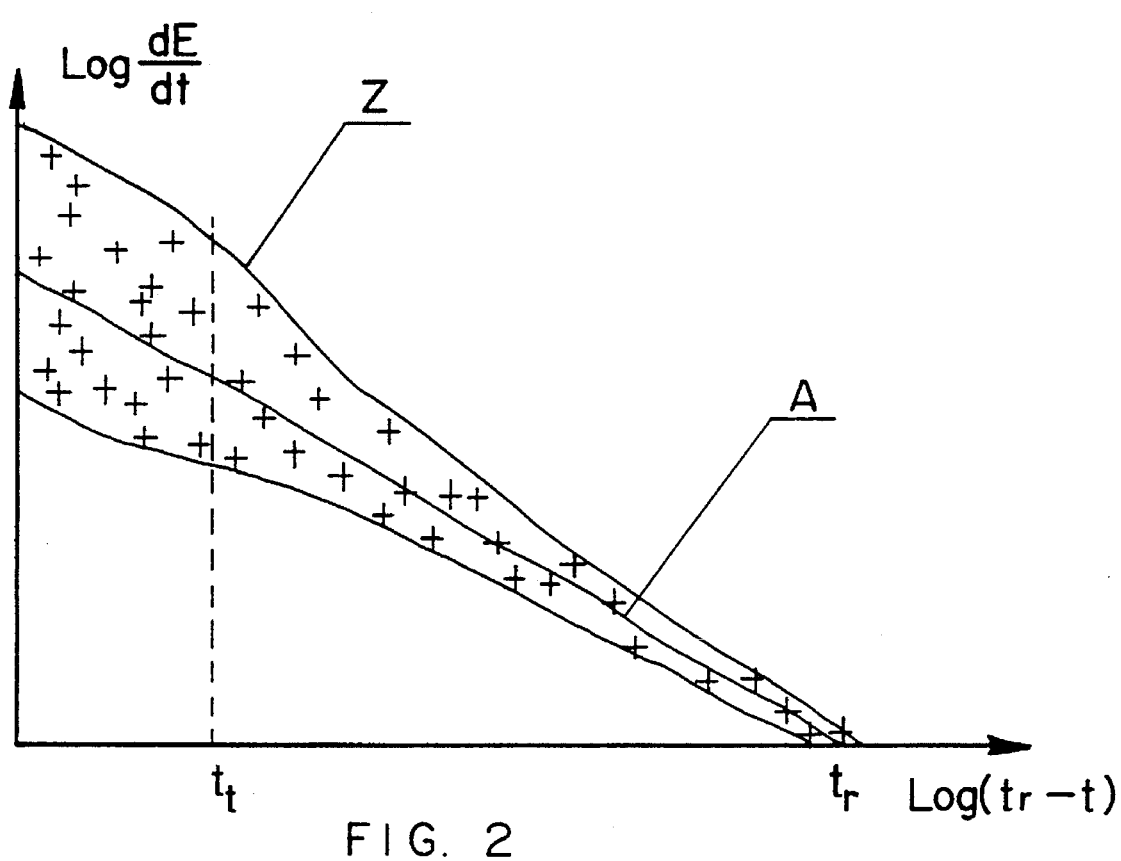
FIG. 2 illustrates the translation of the relationship represented in FIG. 1 into Log-Log coordinates.

The transcription into Log-Log coordinates of the relationship illustrated by FIG. 1 is represented in FIG. 2.

In such FIG. 2, it is observed that threshold excesses or hits, in the sense defined hereinabove as regards inspection techniques via acoustic emissions, are more and more disordered the further one is from the rupture. In other words, as can be noted in FIG. 2 in the portion on this side of the time $t_r$ that corresponds to the test pressure reaching the testing or design pressure value of the tank, the hits are dispersed within a relatively wide zone z, the zone shrinking as and how one comes nearer to the time $t_r$, the entire hits zone being spread along a rectilinear axis A whose equation is given precisely by the relationship:

$Log(dE/dt) = -\alpha\ Log\ (t_r - t) + Log\ (Eo)$.

The determination of the perpendicular A enables Eo to be obtained, which is the original ordinate and $\alpha$, which is the slope.

From now on, from the moment that one has a sufficient cumulative number of hits so as to determine the perpendicular A with an acceptable approximation, one can, well before reaching the time $t_r$ at which point the tank is destroyed, stop the process of subjecting the tank to increasing pressure and predict, via calculation, by a non-linear regression having three parameters Eo, $\alpha$ and $t_r$, or a linear regression by the relationship:

$$\text{Log}(dE/dt) = -\alpha \text{ Log } (t_r - t) + \text{Log }(Eo),$$

the value of $t_r$, i.e., since a known relationship exists between the time and the pressure applied to the tank, the rupture pressure of the tank.

This relationship can be linear, but it can also be otherwise in accordance with the operating protocol selected.

It is important to note that tanks that can be considered as families of objects, the families differentiating themselves from one another by parameters such as the nature of the component materials, the geometries and dimensions of the tanks, the value of $\alpha$ in the relationship defined hereinabove will be the same for tanks having the same representative parameters, such that $\alpha$ can be considered in a way to be the image of each family of tanks.

FIG. 2 shows that the determination of the perpendicular A will be all the more precise the nearer one is to the rupture threshold, the zone z getting increasingly narrower and getting increasingly identified with the perpendicular A.

However, the advantage of the process is to stop the test pressure at a value that is as far away as possible from the rupture value. However, it should not be too far, for example, this side of the design pressure corresponding to the time $t_l$ of FIG. 2, as this would lead to a substantial uncertainty in the determination of the perpendicular A.

Figure 3:
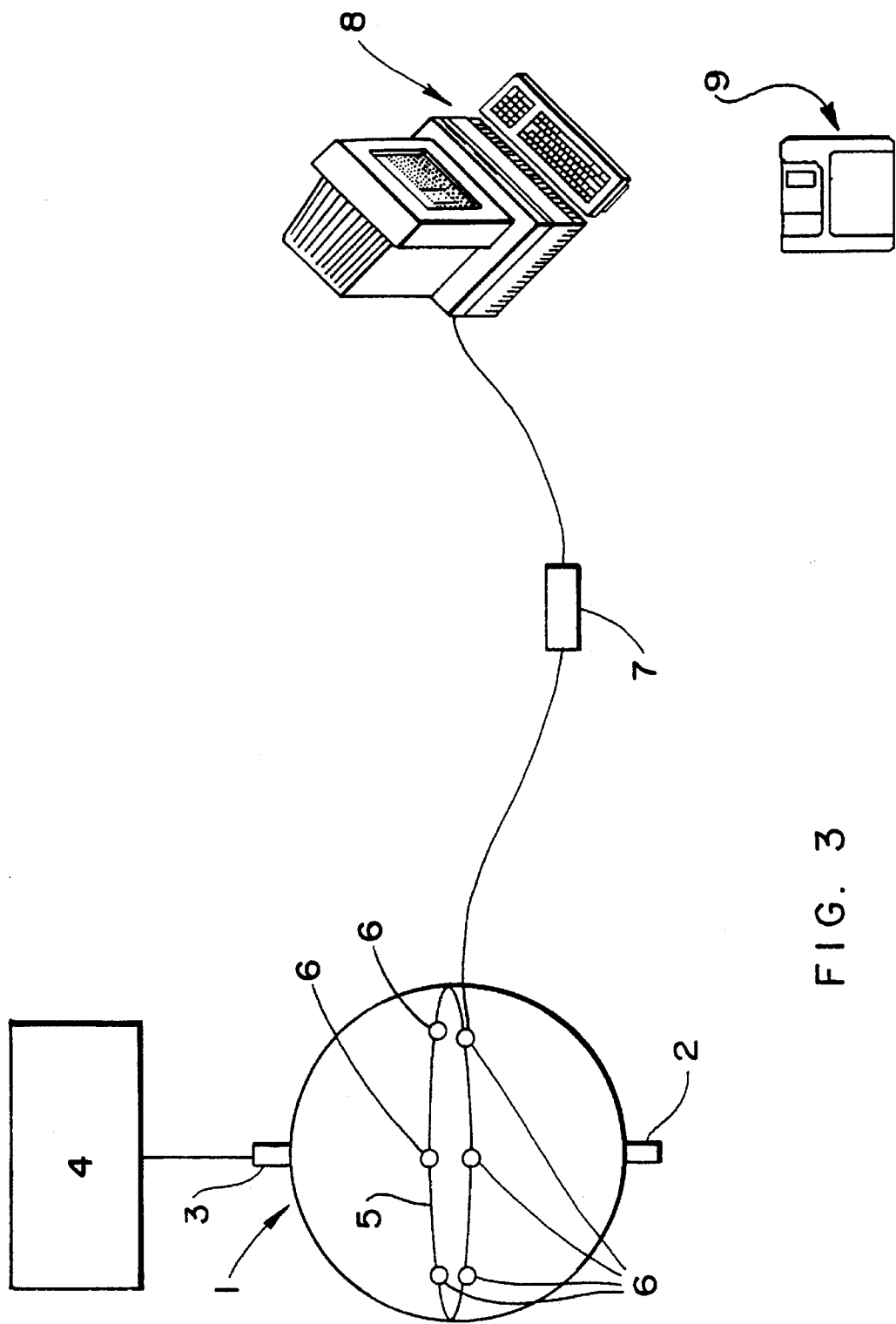
FIG. 3 is a diagram of a device for implementing the method of the invention.

FIG. 3 is a very schematic illustration of an embodiment of the method as per the invention applied to a spherical tank 1 of the composite type wound on a metallic liner.

This tank 1 has two ends, one of which (2) is blocked and the other (3) is connected, in a known manner, to an appropriate conventional hydraulic test installation, represented by the reference numeral 4, the tank being, also in a known manner, maintained by a non-represented appropriate support structure.

Tank 1 is, for example, cinched at the level of the equator by a chain 5 of six piezo-electrical sensors 6, offset angularly by 60°, such an arrangement being similar to the one used in the classic technique of inspection by acoustic emissions.

The tank is located in a test ditch (not represented) and chain 5 is connected, by means of a preamplifier 7 to a recording device 8 of acoustic emissions, at a remote location.

The device 8 is, for example, an acoustic emission acquisition system of the type LOCAN AT marketed by the firm EURO PHYSICAL ACOUSTICS, having an adequate acquisition speed of the acoustic events (several hundreds of events per second) and comprising a number of paths at least equal to the number of sensors 6.

The protocol for pressure increase, recording of the acoustic emission, events thresholding, hits cumulation, is similar to the one used in conventional techniques for non-destructive inspection via acoustic emissions, as mentioned hereinabove.

Such an apparatus, whose main adjustments (threshold, gain, Peak Definition Time, Hit Definition Time, Hit lockout Time) are defined for each test, provides upon exiting each event, the time, pressure, number of hits, energy and amplitude.

These data are recorded in a file 9 that is processed off-line by means of appropriate computer equipment. Such processing consists of evaluating dE/dt, calculating Log(dE/dt) over time, determining the exponent and calculating the rupture pressure.

The method of the invention can be applied to any tank or structure whose rupture pressure one wishes to know and enables such rupture pressure to be predicted for each structure with remarkable precision.

In addition, the method as per the invention having enabled one to verify that, for a predetermined type of structure, the rupture pressure was located in a well circumscribed range of values, it becomes possible to reduce, during construction, the safety coefficients, resulting in a reduction both of the weight of the structure, having equal capacity, as well as manufacturing costs.

The invention finds an application in any structure subjected to a pressure, internal or external, and generally speaking, to any structure subject to mechanical stresses, it being understood that the stress used for acoustic monitoring applied in accordance with the method as per the invention is of the same type as that for which the structure was designed.

The present disclosure relates to subject matter contained in French application no. 94.01237, filed Jan. 31, 1994, whose priority is claimed, and the disclosure of which is incorporated by reference in its entirety.

We claim:

1. Method for predictive determination of load, simple or combined, at rupture, of a structure, comprising:

(a) subjecting the structure to a stress which is equivalent to the load;

(b) while performing step (a), recording acoustic activity generated by damages suffered in the structure, up until a predetermined stress threshold; and (c) determining the predictive value of the load at rupture using the recorded acoustic emission based on a relationship linking time to the load:

$dE/dt = Eo/(t_r - t)^\alpha$ in which:

dE/dt is the variation of acoustic energy generated by the damages;

Eo is a standardizing factor;

t is time, and $t_r$ is the moment of rupture, the exponent $\alpha$, Eo and $t_r$ being determined from the relationship $$\text{Log }(dE/dt) = -\alpha \text{Log }(t_r - t) + \text{Log }(Eo).$$

2. The method as defined by claim 1, wherein the structure comprises a tank made of a composite material wound on a metallic liner.

3. The method as defined by claim 2, wherein the stress which is equivalent to the load is a monotonous pressure increasing to the predetermined stress threshold.

4. The method as defined by claim 2, wherein the stress which is equivalent to the load is a testing pressure in accordance with a predetermined protocol.

5. The method as defined by claim 4, wherein the testing pressure is a monotonous pressure increasing up until the predetermined stress threshold.

6. A method for determining a predicted load, simple or combined, on a structure at rupture, comprising:

(a) subjecting the structure to a stress at a first predetermined level;

(b) incrementally increasing said stress over time from said first predetermined level to a second predetermined level;

(b) recording acoustic emissions generated by damages in the structure, from said first predetermined level to said second predetermined level; and (c) calculating said predicted value of the load at rupture from said recorded acoustic emissions using a predefined formula.

7. The method as defined by claim 6, wherein the structure comprises a tank made of a composite material wound on a metallic liner, and wherein the stress is a monotonous pressure increasing to second predetermined level.

8. The method as defined by claim 6, wherein said formula is a non-linear regression.

9. The method as defined by claim 8, wherein said non-linear regression includes parameters comprising a standardizing factor, the time of rupture, and slope.

10. The method as defined by claim 6, wherein said formula is a linear regression.

11. The method as defined by claim 10, wherein said linear regression is a relationship between time and pressure applied to the tank.

12. The method as defined by claim 6, wherein said formula is defined:

$$dE/dt = Eo/(t_r - t)^\alpha$$

wherein:

dE/dt represents a variation of acoustic energy generated by the damages;

Eo represents a standardizing factor;

t represents time; and $t_r$ represents a time of rupture; and wherein values for exponent $\alpha$, Eo and $t_r$ are determined from the relationship:

$$\text{Log}(dE/dt) = -\text{Log}(t_r - t) + \text{Log}(Eo).$$

13. The method as defined in claim 1, wherein the stress which is equivalent the load comprises an applied stress, of the same type as the load, applied to the structure under test, the applied stress increasing according to a predetermined relationship with respect to a duration of time that the applied stress is applied.

* * * * *